United States Patent [19]
Miura et al.

[11] 3,946,308
[45] Mar. 23, 1976

[54] DIELECTRIC APPARATUS AND METHOD UTILIZING RESONANCE FOR HUMIDITY MEASUREMENT

[75] Inventors: Taro Miura; Takahiro Yamamoto, both of Tokyo, Japan

[73] Assignee: TDK Electronics Co., Ltd., Tokyo, Japan

[22] Filed: Nov. 25, 1974

[21] Appl. No.: 527,072

[30] Foreign Application Priority Data
Nov. 27, 1973 Japan.............................. 48-132138

[52] U.S. Cl.............................. 324/58.5 C; 73/336
[51] Int. Cl.² G01R 27/26; G01R 27/04; G01W 1/00
[58] Field of Search..... 324/58.5 R, 58.5 A, 58.5 C; 73/29, 335, 336, 336.5

[56] References Cited
UNITED STATES PATENTS

| | | | |
|---|---|---|---|
| 2,792,548 | 5/1957 | Hershberger | 324/58.5 C |
| 2,882,493 | 4/1959 | Dicke | 324/58.5 C |

OTHER PUBLICATIONS

Jaeger et al., "Microwave Measurements of the Loss in Low Loss Dielectrics," *Rev. of Sci. Instruments,* Vol. 41, June 1970, pp. 820–823.
Magee et al., "Recording Microwave Hygrometer," *Rev. of Sci. Instruments,* Vol. 29, Jan. 1958, pp. 51–54.
Berliner et al., "Phase-Sensitive Ultrahigh-Frequency Moisture Gauge," Ind. Lab(USA), Vol. 37, Oct. 1971, pp. 1624–1626.

*Primary Examiner*—Alfred E. Smith
*Assistant Examiner*—Wm. H. Punter
*Attorney, Agent, or Firm*—Cooper, Dunham, Clark, Griffin & Moran

[57] ABSTRACT

Apparatus for humidity measurement employing a dielectric resonator consisting essentially of a metallic guard, a solid dielectric material, an input antenna and an output antenna.

Method of measuring humidity comprising feeding a microwave energy of swept frequencies to the input antenna of said apparatus, recovering said energy as a microwave power from the output antenna, and then determining the humidity of the gas through which the microwave energy travels from one antenna to the other, the value of humidity being based on the frequency characteristic of said microwave power.

9 Claims, 8 Drawing Figures

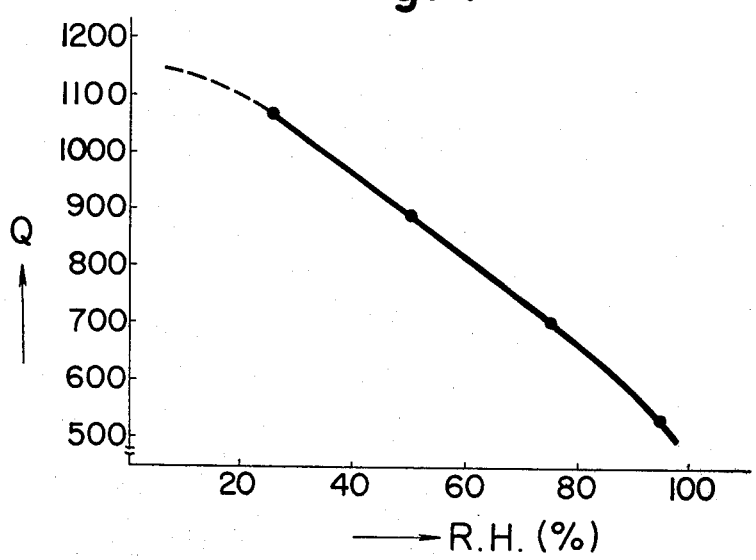

DIELECTRIC APPARATUS AND METHOD UTILIZING RESONANCE FOR HUMIDITY MEASUREMENT

BACKGROUND OF THE INVENTION

1. Field of the Invention

This invention relates to the apparatus and method utilizing ultra-high frequency or microwave energy for the purpose of measuring the humidity in a gas such as air.

2. Description of the Prior Art

Instruments of humidity measurement, generally known as hygrometers, are many in kind and have long been in use. Examples are:

1. A hair hygrometer, in which measurement is based on the contraction and extension of hair in proportion to changes in humidity;
2. a dew point hygrometer, which produces a humidity measurement by directly detecting the dew point of a gas under investigation;
3. a psychrometer, which measures the weight of the water vapor contained in a gas;
4. Assamann's aspiration psychrometer, which provides humidity measurements by aspiration;
5. an absorption hygrometer, in which humidity measurements are produced from the change in electric resistance of a hygroscopic material with humidity.

It is well known that the above-mentioned instruments are not accurate in measurement, unreliable in measuring operation and difficult to maintenance properly. The humidity information made available from these instruments is not in the form of electrical signal and, therefore, cannot be utlized as an input signal to any automatic control device.

Recently a humidity measurement system was proposed. It is a system employing two cavity resonators. Its measuring operation is based on the fact that the humidity of air effects the transmission characteristic of an ultra-high-frequency signal of the kind commonly known as microwave. The gas, whose humidity is to be checked, is contained in one resonator and dry air is contained in the other. A microwave of the desired mode and frequency is fed into the two resonators to produce a resonant condition in each. Since the amount of water contained in the gas under investigation or, simply, the humidity increases the dielectric constant or permittivity of of the gas, there occurs a difference in resonant frequency between the two cavity resonators. This difference, that is, "beat" frequency is measured to tell the humidity in the gas.

This recently proposed system too has drawbacks in that the detector circuitry for finding out the value of said beat frequency is necessarily complex to result in a high manufacturing cost, and that the temperature changes of the two resonators must be taken into consideration to accurately measure the respective resonant frequencies if the measuring error due to temperature changes is to be reduced to an extent necessary for practical humidity measurement. Thus, the devices for this system are inevitably complicated and expensive.

SUMMARY OF THE INVENTION

It is an object of this invention to provide an improved method of humidity measurement and also an apparatus for implementing said method which is composed of devices small in size, very light in weight, simple in mechanical construction, and low in manufacturing cost.

BRIEF DESCRIPTION OF THE DRAWINGS

FIG. 4 graphically shows the relationship between Q value and relative humidity.

DETAILED DESCRIPTION OF THE PREFERRED EMBODIMENTS

Figure 1A:
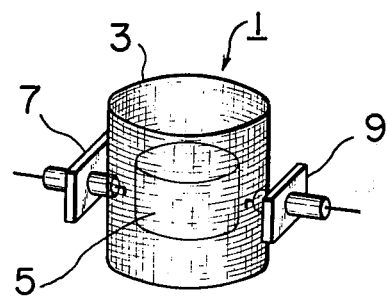
FIG. 1(a) is a perspective view of the apparatus according to this invention.
Figure 1B:
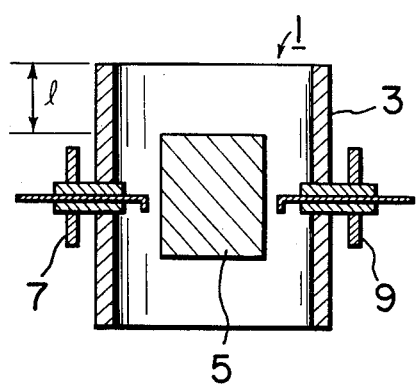
FIG. 1(b) is a section view of apparatus illustrating this invention.
Figure 1C:
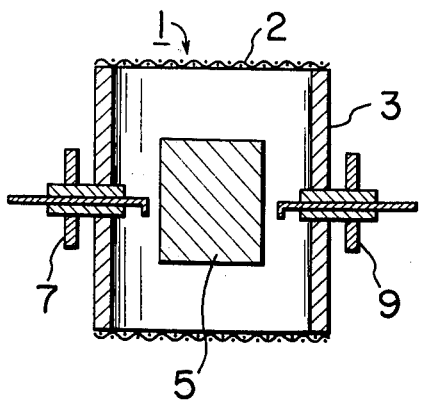
FIG. 1(c) is a section view of the apparatus of still another embodiment of this invention.

Embodiments of this invention are represented in the attached drawings, in which FIG. 1(a) is a perspective view of the apparatus using a copper wire net as the cylindrical guard; FIG. 1(b) is a section view of apparatus using a brass cylindrical guard illustrating representative dimensions; and FIG. 1(c) is a section view of the apparatus of FIG. 1(b), in which the cylindrical brass guard has its top and bottom ends covered by copper-wire-net lids.

Referring first to FIG. 1(a), resonator 1 is of dielectric type comprising a cylindrical guard 3 made of copper wire net, about 1 mm in wire diameter, a solid dielectric body 5 situated within said guard, an input antenna 7 and an output antenna 9, the two antennas being mounted in apposition on said guard.

When this resonator is to be operated with a microwave frequency of, say, 10.7 GHz to resonate in TE mode, the cylindrical guard 3 must have its radius sized smaller than the cutoff radius, for dominant mode or the lowest mode, of a cylindrical waveguide at 10.7 GHz. The smaller radius is for curbing the loss by emission of microwave energy into free space in order to minimize the variation or instability of humidity measurement due to the effect of microwave energy loss. Specifically, this inventor selected a radius of 0.9 cm for guard 3, a value smaller than the cutoff radius, which is 1.07 cm, for $TM_{01}$ mode at 10.7 GHz.

Dielectric body 5 is titanium oxide ($TiO_2$) in material, whose dielectric properties are characterized by a speific inductive permittivity (relative permittivity) $\epsilon_r$ of 100 and an electrical quality factor $Q_e$ of 2000. This body is sized 0.25 cm in radius and 0.2 cm in height. For antennas 7, 9, the core conductor of a coaxial cable stripped of its outer conductor or sheath is used, the core being a tin-plated copper wire 0.5 mm in diameter.

With a 10.7-GHz microwave energy is passed into dielectric resonator 1 through its input antenna 7, a resonant oscillation is induced in this resonator. This oscillation is of such field configuration similar to the $TM_{110}$ mode of cylindrical resonators, and makes available from antenna 9 a microwave output power.

If resonator (1) is placed in an atmosphere of humid air, the quality factor Q of its resonant circuit falls, because water vapor absorbs the microwave energy in resonance. Thus, such a quality factor Q can be a measure of the amount of water contained in the air, that is, humidity. There are many known methods of measuring the Q of a resonant circuit. One method is based on conversion of the half-value width of microwave power into a pulse width. This method is employed in the present embodiment.

Referring to FIG. 1(b), useful in illustrating representative dimensions, the dielectric resonator is constructed differently in that its cylindrical guard is made of a brass cylinder. As in the case of the resonator of FIG. 1(a), the radius of the cylindrical guard is smaller than the cutoff raidus at the operating frequency for the purpose already stated. Note that the distance $l$ is provided between the dielectric body and the upper end of the guard. This distance is for accomplishing the stated purpose more effectively, that is, to minimize the escape of microwave energy from the cylindrical guard. This inventor gave 3 mm to this distance $l$. The separation of the dielectric body from the guard is desirable also for the resonators of FIGS. 1(a) and (c).

Referring now to FIG. 1(c), wherein another construction of the resonator is shown. Note that the resonator is identical in construction to the one shown in FIG. 1(b) except for its top and bottom being covered by lids made of a copper wire net. These lids are for keeping out dust and foreign matters.

How the dielectric resonator is operated in the humidity measuring apparatus of this invention will be described by referring to FIG. 2, in which a simplified block diagram represents the embodiment. Block 11 is a swept-frequency oscillator of known type, whose oscillation is produced by the Gunn effect and whose oscillating frequency is linearly swept or varied with time from the center frequency of 10.7 GHz upward and downward in a cyclical manner. Its output is a swept-frequency microwave energy, which is admitted into said dielectric resonator 1 through the input antenna. The microwave output power available from the output antenna is proportional in magnitude to the input energy. This output power is picked up and then detected, in the manner of demodulation, by diode detector 13. Since the microwave input power coming from oscillator 11 consists of the frequencies arising from the center frequency being linearly and regularly swept upward and downward, the detected output of diode detector (13) is in such a waveform as shown in FIG. 3(a), in which the horizontal axis is a frequency scale and the vertical axis is a power amplitude scale. The peak value of amplitude occurs at 10.7 GHz in the waveform of FIG. 3(a), and the frequency at which the amplitude equal one-half of the peak value, meaning a drop of 3 dB, occurs at both sides of the 10.7-GHz center frequency, the distance on the horizontal axis from the center to each of the two points is the half-value frequency width, $\Delta f_1$, the value of which determines the Q value of the resonant frequency in the dielectric resonator. The output of detector 13 is passed onto differentiator 17 through amplifier 15.

Figure 3A:
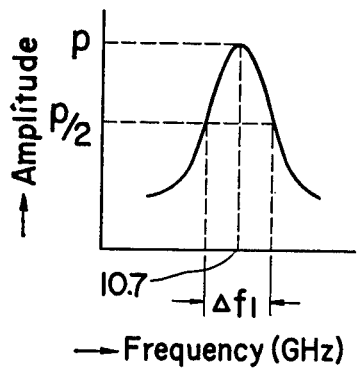
FIGS. 3(a), (b) and (c) show the waveforms available from the apparatus of FIG. 2.
Figure 3B:
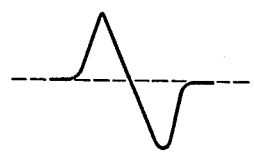
Figure 3C:
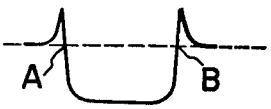

In differentiator 17, the input signal is differentiated twice with respect to time to change into the shape as shown in FIG. 3(c). The waveform shown in FIG. 3(b) is what results from the first differentiation. In the waveform of FIG. 3(c), let A represent the frequency corresponding to the moment at which the differentiated output voltage becomes zero during fall and B the frequency corresponding to the moment at which the voltage becomes zero during rise. Then, $B - A = \Delta f_2$, where $\Delta f_2$ is a frequency width. Where the crystal diodes of detector 13 have a voltage squaring characteristic to give a square-law detection capability to this detector, then, as is well known, the half-value width $\Delta f_1$ of the dielectric resonator and the frequency width $\Delta f_2$ are related according to this equation:

$$\frac{\Delta f_2}{\Delta f_1} = \frac{1}{\sqrt{6}}$$

With the value of $\Delta f_2$ determined by measurement, the above equation gives the value of $\Delta f_1$ and, since $Q = \Delta f_o/\Delta f_1$, the Q of the resonant circuit can be determined. In the present case, $f_o$ is the center frequency of 10.7 GHz.

Actually, the voltage output of differentiator 17 is fed into pulse-width measuring circuit 19, whose output is proportional to $\Delta f_2 = B - A$. This output signal is used to drive indicator (21) calibrated to indicate the humidity and, additionally, is transmitted out as a control signal.

The graph of FIG. 4 shows the results obtained from an experimential operation of the apparatus constructed and arranged according to the foregoing embodiment of this invention, with the values of Q plotted on the vertical axis, the horizontal axis being calibrated in per-cent relative humidity.

The foregoing description of an embodiment of this invention presumes the humid gas to be air but this by no means implies that use of the apparatus or method according to this invention is limited to the measurement of humidity in air. Since the measuring operation is founded on detection of a microwave energy attenuation occurring in a gas, the apparatus and method can be applied to any polar gas for humidity measurement. Though use of a guard made of a brass wire net was mentioned in the foregoing description, the guard may be a net of any other metal. The antennas need not be of any special kind; they may be any of those conventionally used in waveguide work.

For the dielectric body located in the path of the microwave energy, $MgTiO_3$, $CaTiO_3$ or any like compound, or any other ceramic dielectric material consisting of any combination of these materials, may be used besides $TiO_2$ mentioned above, provided that they produce a Q value of at least 1000. Even such an organic dielectric material as styrene resin can be used as the material for the dielectric body, whose shape, moreover, is not limited to the cylindrical one cited in the foregoing description.

Obviously many modification and variations of the present invention are possible in the light of the above teachings. It is therefore to be understood that within the scope of the appended claims the present invention may be practiced otherwise than as specifically described above.

Figure 2:
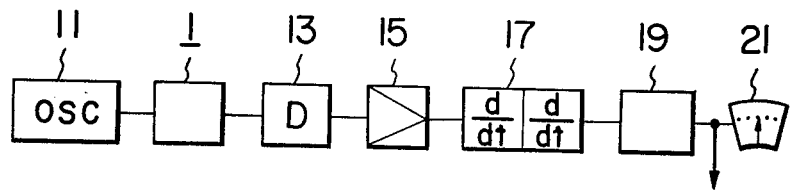
FIG. 2 is a schematic block diagram representing the apparatus of this invention.

A humidity measuring apparatus according to this invention, comprising the series of devices indicated in FIG. 2, inclusive of the dielectric resonator, can be constructed compact and lightweight. Moreover, if a dielectric material with constant temperature characteristics is used for the dielectric body of the resonator, a change, if any, in the frequency characteristic of the resonator itself caused by a change in ambient temperature or any other factor shows up as a corresponding signal change also in the above-mentioned half-value width and, therefore, does not show up as an error in the measured humidity value. From this, it will be seen that the apparatus according to this invention can be made high in measuring accuracy and also in operating reliability as compared with conventional hygrometers.

Further, according to this invention, both relative humidity and absolute humidity can be measured with an added advantage that the response to a humid gas under investigation is quick in the measuring operation.

In contrast particularly to the conventional hygrometers operating by the principles of deliquescence, the apparatus according to this invention lasts long and serves with long life because its operation does not involve any physical contact between surfaces or points and because its components can be made high in interchangeability.

It may be hardly necessary to point out that the measuring sensitivity of the apparatus can be enhanced by comparing the results of each measuring operation against those obtained on a reference gas.

What is claimed is:

1. Apparatus for measuring humidity comprising a dielectric material, a shield against electrical radiant energy surrounding said dielectric material, said shield being in the form of a cylindrical sleeve comprising a wire net, and input and output antenna means positioned inside said shield and spaced from said dielectric material.

2. Humidity measuring apparatus according to claim 1 in which said shield is capped at both its ends by a wire net.

3. Humidity measuring apparatus according to claim 1 in which said input antenna means is adapted to receive an input electrical signal sweeping through a range of frequencies about a center frequency, and the radius of said shield is smaller than the cutoff radius of a cylindrical waveguide operating in its dominate mode at said center frequency.

4. Humidity measuring apparatus according to claim 1 in which said dielectric material is in the form of a solid cylinder.

5. Humidity measuring apparatus according to claim 1 in which said shield is of copper or brass.

6. Humidity measuring apparatus according to claim 1 in which said dielectric material is a ceramic dielectric material.

7. Humidity measuring apparatus according to claim 1 in which said dielectric material is positioned between said input and output antenna means.

8. In combination with humidity measuring apparatus according to claim 1, means coupled to said input antenna means for applying thereto an input electrical signal sweeping through a range of frequencies about a center frequency, and output means coupled to said output antenna means for developing an ouput electrical signal representing the humidity within said shield.

9. Humidity measuring apparatus according to claim 8 in which said output means includes detector means coupled to said output antenna means for developing a detected signal in response to signals received from said output antenna means, differentiator means for differentiating the signal developed by said detector means and generating a pulse signal therefrom, and pulse width measuring means for generating a signal representative of the width of pulses in said pulse signal.

* * * * *